United States Patent
Dikstein

(10) Patent No.: US 10,660,961 B2
(45) Date of Patent: *May 26, 2020

(54) METHOD OF TREATMENT OF IRRITATION OF SKIN OR MUCOUS CELLS

(71) Applicant: RESDEVCO RESEARCH AND DEVELOPMENT CO. LTD., Jerusalem (IL)

(72) Inventor: Shabtay Dikstein, Jerusalem (IL)

(73) Assignee: RESDEVCO RESEARCH AND DEVELOPMENT CO., LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/687,600

(22) Filed: Aug. 28, 2017

(65) Prior Publication Data

US 2017/0354735 A1    Dec. 14, 2017

Related U.S. Application Data

(62) Division of application No. 11/914,429, filed as application No. PCT/IL2006/000537 on May 7, 2006, now abandoned.

(30) Foreign Application Priority Data

May 16, 2005   (IL) .......................... 168603

(51) Int. Cl.
| | |
|---|---|
| A61K 47/32 | (2006.01) |
| A61K 8/34 | (2006.01) |
| A61K 8/42 | (2006.01) |
| A61K 9/00 | (2006.01) |
| A61K 47/10 | (2017.01) |
| A61K 47/18 | (2017.01) |
| A61K 47/26 | (2006.01) |
| A61Q 19/00 | (2006.01) |

(52) U.S. Cl.
CPC .............. *A61K 47/32* (2013.01); *A61K 8/345* (2013.01); *A61K 8/42* (2013.01); *A61K 9/0014* (2013.01); *A61K 9/0048* (2013.01); *A61K 47/10* (2013.01); *A61K 47/18* (2013.01); *A61K 47/183* (2013.01); *A61K 47/26* (2013.01); *A61Q 19/00* (2013.01); *A61K 2800/75* (2013.01)

(58) Field of Classification Search
None
See application file for complete search history.

(56) References Cited

FOREIGN PATENT DOCUMENTS

| | | | |
|---|---|---|---|
| EP | 1354580 | * | 10/2003 |
| JP | 2003-20593 A | | 1/2003 |
| JP | 2003020593 | * | 1/2003 |

OTHER PUBLICATIONS

Monika-Hildegard Schmid-Wendtner; Korting Schmid-Wendtner (2007). Ph and Skin Care. ABW Wissenschaftsverlag. pp. 31.*
Zlotogorski A (1987). "Distribution of skin surface pH on the forehead and cheek of adults". Arch. Dermatol. Res. 279 (6): 398-401.*
Schmid MH, Korting HC (1995). "The concept of the acid mantle of the skin: its relevance for the choice of skin cleansers" (PDF). Dermatology, Abstract, 191 (4): 276-80.*
Machine Translation of JP 2003020593 at https://patents.google.corn/patent/JP2003020593A/en?oq=2003020593#similarDocuments, downloaded Jun. 13, 2019 from the internet (Year: 2003).*
Database Caplus Chemical Abstracts Service, Columbus, Ohio, US; Database Accession No. 2003:56425, Abstract of JP 2003020593, Kono K. K., Japan; Kawano Paper Co., Ltd., Kono et al., Dec. 4, 2003 (Year: 2003).*
Machine Translation of KR 1999-0077866 (Year: 1999).*

* cited by examiner

Primary Examiner — Karl J Puttlitz

(57) ABSTRACT

The present invention provides a method of treatment of irritation of skin or mucous cells. The method comprises applying topically a composition comprising a combination of: xylitol, myonisotiol or mannitol or any combination of these; glycerol and/or urea; water; in the absence of any oil in water or wax in water emulsion.

19 Claims, No Drawings

METHOD OF TREATMENT OF IRRITATION OF SKIN OR MUCOUS CELLS

CROSS REFERENCE TO RELATED APPLICATIONS

This application is a Divisional Application of U.S. patent application Ser. No. 11/914,429, filed Nov. 14, 2007, which is a National Phase Entry of International (PCT) Patent Application No. PCT/IL2006/000537, filed May 7, 2006, and claims priority from Israel Patent Application No. 168603, filed May 16, 2005, all of which are hereby incorporated by reference.

FIELD AND BACKGROUND OF THE INVENTION

The present invention provides a new combination of topically active substances, for the prevention and alleviation of cell damage, caused by preservatives, detergents or drugs, used in topical pharmaceutical, cosmetic or veterinary compositions.

Many substances are applied topically to the skin or mucous membranes of humans or animals in order to alter the subject's appearance, to protect the subject from the environment, or to produce a biological change in the skin or other tissue for therapeutic, preventive or cosmetic purposes. These substances may generically be termed "topical products" and include such topically applied substances as cosmetics, over-the-counter and prescription topical drugs, and a variety of other products such as soaps and detergents.

Topical products occur in a variety of forms, including solids, liquids, suspensions, semisolids (such as creams, gels, pastes or "sticks"), powders or finely dispersed liquids such as sprays or mists. Examples of topical products commonly classified as "cosmetics" include skin care products such as creams, lotions, moisturizers and "treatment cosmetics" such as exfoliants and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions; bath products such as oils; eye care products such as eye lotions and makeup removers; foot care products such as powders and sprays; skin colorant and make-up products such as foundations, blushes, rouges, eye shadows and liners, lip colors and mascaras; lip balms and sticks; hair care and treatment products such as shampoos, conditioners, colorants, dyes, bleaches, straighteners and permanent wave products; baby products such as baby lotions, oils, shampoos, powders and wet wipes; feminine hygiene products such as deodorants and douches; skin or facial peels applied by dermatologists or cosmeticians; and others. Examples of topical products commonly classified as "topical drugs" are many and varied, and include over-the-counter and/or prescription products such as antiperspirants, insect repellents, sunscreens and sunburn treatments, anti-acne agents, antibiotics, topical respiratory agents, ocular drugs such as eyedrops and saline solutions, therapeutic retinoids, anti-dandruff agents, external analgesics such as capsaicin products, topical contraceptives, topical drug delivery systems, gastrointestinal agents such as suppositories, enemas and hemorrhoid treatments, reproductive system agents such as vaginal treatments, oral treatments such as lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

In a large number of cases topical products contain chemicals which may produce "irritation," including various inflammation symptoms or signs, when applied to the skin or mucosa. The present invention is directed to compositions for inhibiting the irritation associated with such topical products.

The occurrence, frequency and nature of topical-product-induced irritation often varies from user to user. The severity of irritation to the susceptible user may range from subclinical to mild to severe. Typical symptoms of "irritation" include itching (pruritus), stinging, burning, tingling, "tightness," erythema (redness) or edema (swelling). The irritation response may be due to the direct effect on the skin of certain topical product chemicals or to a response by the immune system directed toward the chemicals alone or in combination with skin components (e.g. antigens).

Many ingredients used in topical products are known irritants or are potentially irritating, especially to people with "sensitive skin". These irritating ingredients include fragrances, preservatives, solvents, propellants and many other ingredients that might otherwise be considered inert components of the products. Additionally, many topical product active ingredients, including chemicals that may also be classified as drugs, produce irritation when applied to the skin. These include, but are not limited to, such ingredients as exfoliants and skin cell renewal agents, anti-acne drugs, antiperspirant compounds, antihistamines, anti-inflammatory agents, skin protective agents, insect repellent chemicals, sunscreens and many others. Where more than one chemical irritant is present, their irritating effects may be additive. Furthermore, chemical ingredients may react with one another, or in the environment of the skin, to form new chemicals which are irritating. The vehicles in which the active drug ingredients are formulated may also produce irritation in sensitive people.

Whatever the exact cause of irritation, many attempts have been made to reduce the irritation potential of topical products by identifying chemicals which tend to cause irritation and reducing their concentration or eliminating them from the products. Many of these products are advertised to consumers as "hypoallergenic" or the like to designate a product's reduced tendency to cause irritation in consumers with sensitive skin. Many skin and mucosal irritation responses, however, are not allergic in origin. In any event, it is often not feasible or practical to identify or eliminate all of the irritating chemical(s), particularly when the irritating chemical(s) are the active ingredient of the product or are required for formulation, preservative or other functional reasons.

It is an object of the present invention to provide an effective topical composition, for combating damaging effects of irritants to mucous and skin cells.

The present invention relates to topical compositions for combating damaging effects of preservatives or other irritants, found, e.g. in multi-dose eye drops, to mucous cells, especially in the corneal cells and simultaneously beneficial to those tissues. It was found that glycerol counteracts corneal cell damage caused by preservatives such as benzalkonium chloride, cetrimonium bromide, sodium ethylene diamine tetraacetate, etc. Not all the polyhydroxy compounds have such anti-irritant properties. Moreover, it is known that isotonic sodium chloride is toxic to the corneal cells, whereas isotonic glycerol is not toxic. (Follmann, P. et. al. Szemeszet 141, 305-308, 2004.)

In addition two physicochemical parameters are very important for a good topical composition: increased viscosity and increased spread of the solution.

Increased viscosity is achieved by high molecular weight (equal to more than 0.5 million Dalton) polymers. Increased spread is achieved by surface active agents, however after chronic use the surface active agents usually have damaging effects. (See Animal Studies, a).

It has now been found according to the present invention that all of the above mentioned problems of irritation by preservatives, detergents and other cell damaging agents disappear, and the beneficial effects are preserved or increased, by using a combination of xylitol, myoinositol or mannitol with glycerol and/or urea, preferably together with a surface active agent.

The advantages resulting from the addition of a surface active agent include a decrease in the surface tension of the aqueous solution, thereby increasing the spread. Thus it has now been found, that polysorbate 90 even at a concentration of 0.002% increases the diminished Break Up Time (BUT) in dry eye patients. (It is accepted that 10 sec. or less BUT indicates dry eye syndrome) (See Human Studies 1).

Thus, according to the present invention there are now provided topical pharmaceutical or cosmetic compositions for the prevention and treatment of irritation of mucous cells, or skin cells, comprising a combination of:
xylitol, myoinositol or mannitol or any combination of these;
glycerol and/or urea;
water;
in the absence of any oil in water or wax in water emulsion.

The present invention provides topical pharmaceutical or cosmetic compositions for the prevention and treatment of irritation of mucous cells, comprising a combination of:
1.5-5.5% xylitol, myoinositol or mannitol or any combination of these;
0.9-2.0% glycerol;
less than 0.01% inorganic salts;
water;
in the absence of any oil in water or wax in water emulsion.

The present invention further provides topical pharmaceutical or cosmetic compositions, for the prevention and treatment of irritation of skin cells, comprising a combination of:
5-18% xylitol, myoinositol or mannitol or any combination of these;
5-10% glycerol and/or urea;
water;
in the absence of any oil in water or wax in water emulsion.

More specifically the present invention preferably provides a non-irritant topical cosmetic or pharmaceutical composition for mucous cells or for the skin, as defined above, for the prevention of cell damage caused by preservatives, detergents or drugs in topically used cosmetic, pharmaceutical or veterinary compositions.

In especially preferred embodiments of the present invention there is provided a non-irritant topical cosmetic or pharmaceutical composition for mucous cells or for the skin, as defined above, further comprising at least one pharmaceutically active agent in solution, or in suspension but not in emulsion.

In preferred embodiments of the present invention there is provided a non-irritant topical cosmetic or pharmaceutical composition for mucous cells or for the skin, as defined above, further comprising at least one viscosity enhancing agent.

While the invention will now be described in connection with certain preferred embodiments in the following examples so that aspects thereof may be more fully understood and appreciated, it is not intended to limit the invention of these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of proving what is believed to be the most useful and readily understood description of formulation procedures as well as of the principles and conceptual aspects of the invention.

EXAMPLES

Example 1

Moisturizing Eye Drops

| | |
|---|---|
| Sodium hyaluronate | 0.03 gm. |
| Povidone | 2.0 gm. |
| Glycerol | 1.0 gm. |
| Mannitol | 3.2 gm. |
| Cetrimide | 0.01 gm. |
| NaOH | q.s. to pH 7.0 |
| $H_2O$ | to 100 ml. |

Example 2

Moisturizing Eye Drops

| | |
|---|---|
| Glycerol | 1.3 gm. |
| Xylitol | 2.2 gm. |
| Benzalkonium Chloride | 0.01 gm. |
| NaOH | q.s. to pH 7.0 |
| $H_2O$ | to 100 ml. |

Example 3

Moisturizing Eye Drops Unit Dose Form for Single Application

| | |
|---|---|
| Sodium hyaluronate | 0.03 gm. |
| Povidone | 2.0 gm. |
| Glycerol | 1.0 gm. |
| Myoinositol | 3.2 gm. |
| Cetrimide | 0.01 gm. |
| NaOH | q.s. to pH 7.0 |
| $H_2O$ | to 100 ml. |

Example 4

Moisturizing Anti-Inflammatory Eye Drops

| | |
|---|---|
| Glycerol | 1.3 gm. |
| Xylitol | 2.2 gm. |
| Sodium diclofenac | 0.1 gm. |
| NaOH | q.s. to pH 7.2 |
| H₂O | to 100 ml. |

Example 5

Moisturizing Anti-Inflammatory Eye Drops Unit Dose for Single Application

| | |
|---|---|
| Glycerol | 1.0 gm. |
| Mannitol | 1.6 gm. |
| Xylitol | 1.6 gm. |
| Sodium diclofenac | 0.1 gm. |
| NaOH | q.s. to pH 7.2 |
| H₂O | to 100 ml. |

Example 6

Moisturizing Gel for Skin

| | |
|---|---|
| Glycerol | 8.0 gm. |
| Mannitol | 5.0 gm. |
| Urea | 5.0 gm. |
| Glycine | 5.0 gm. |
| Methylparaben | 0.1 gm. |
| Propylparaben | 0.01 gm. |
| Polyacrylate 980 adjusted to pH 4.5 | 0.7 gm. |
| H₂O | to 100 ml |

Example 7

Moisturizing Gel for Skin

| | |
|---|---|
| Glycerol | 10.0 gm. |
| Xylitol | 8.0 gm. |
| Urea | 5.0 gm. |
| Glycine | 5.0 gm |
| Methylparaben | 0.1 gm. |
| Propylparaben | 0.01 gm. |
| Polyacrylate 980 adjusted to pH 4.5 | 0.7 gm. |
| H₂O | to 100 ml |

Example 8

Moisturizing Gel for Skin

| | |
|---|---|
| Glycerol | 8.0 gm. |
| Myoinositol | 4.5 gm. |
| Xylitol | 3.5 gm |
| Urea | 5.0 gm. |
| Glycine | 5.0 gm. |
| Methylparaben | 0.1 gm. |
| Propylparaben | 0.01 gm. |
| Polyacrylate 980 adjusted to pH 4.5 | 0.7 gm. |
| H₂O | to 100 ml |

Example 9

Moisturizing Gel with Phytosphingosine Suspension for Skin

| | |
|---|---|
| Glycerol | 8.0 gm. |
| Xylitol | 7.0 gm |
| Polyethylene glycol 3350 | 2.0 gm |
| Phospholipids | 0.25 gm |
| Phytosphingosine in suspension | 0.2 gm. |
| Polyacrylate 980 or 974 | 1.0 gm. |
| Methylparaben | 0.1 gm. |
| Propylparaben | 0.01 gm. |
| H₂O | to 100 ml |

Suitable preservatives, suspending agents, excipients and other additives can be incorporated. The preferred pH (to be adjusted) of the compositions of examples 6 to 9 is pH 4.0 to 6.0.

Methods:

Human Studies a. 23 dry eye patients received in both eyes 5 drop of Fluorescein-Novesin mixture. After 30 seconds the right eye was treated with 1 drop from the treatment bottle. The patient was asked to blink 2-3 times, then the fluorescein BUT was measured. Afterwards the left eye was treated with 1 drop from the Control bottle, the patient was asked to blink 2-3 times. Then the fluorescein BUT was measured.

Materials: Control—0.9% NaCl (saline); surface tension 72 mN/m

Treatment=as Control+0.002% Tween 80; surface tension 49 mN/m (dyn/cm)

Results:

| Left eye - Control | Right eye - Treatment |
|---|---|
| 7.7 ± 0.4 sec | 12.7 ± 1.5 sec |

Paired differences 5.0 ± 1.4 sec (p~0.001)

b. Examination of Treatment, of Conjunctival Damage, in Dry Eye Syndrome.

One month study, use of the eye drops three times a day:

Left eye=essentially isotonic Glycerol (marketed product) (L).

Right eye=50% isotonic Glycerol+50% isotonic Xylitol®.

| | Rose Bengal Score (Oxford Scale) | | | |
|---|---|---|---|---|
| | Before | | One month | |
| Patient No. | R | L | R | L |
| 1 | 3 | 3 | 1 | 2 |
| 2 | 2 | 3 | 0 | 2 |
| 3 | 2 | 3 | 0 | 2 |

-continued

| | Rose Bengal Score (Oxford Scale) | | | |
|---|---|---|---|---|
| | Before | | One month | |
| Patient No. | R | L | R | L |
| 4 | 3 | 3 | 1 | 2 |
| 5 | 1 | 3 | 1 | 2 |
| mean | 2.2 | 3.0 | 0.6 | 2 |

| | Personal Satisfaction | | | |
|---|---|---|---|---|
| | Before | | One month | |
| Patient No. | R | L | R | L |
| 1 | 0 | 0 | 2 | 1 |
| 2 | 0 | 0 | 2 | 1 |
| 3 | 0 | 0 | 2 | 1 |
| 4 | 0 | 0 | 2 | 1 |
| 5 | 0 | 0 | 2 | 1 |
| mean | 0 | 0 | 2 | 1 |

0 = not satisfied
1 = better
2 = much better

Essentially the same results were obtained, by using Myoinositol instead of Xylitol.

Animal Studies a. 3 rabbits were treated for 3 months twice daily with eye drops, adjusted to pH 7.0. The average cross section of the epithelial corneal cells and the percentage of damaged cells were evaluated by electromicroscopy.

| Treatment | Cross section in μ² | Damaged cells % |
|---|---|---|
| None | 590 | 16 |
| 0.9% NaCl | 542 | 28 |
| 0.01% Benzalkonium Chloride + 0.9% NaCl | 538 | 29 |
| 0.01% Benzalkonium Chloride + 2.5% Glycerol | 699 | 14 |
| 0.01% Cetrimonium Bromide + 0.9% NaCl | 591 | 27 |
| 0.01% Cetrimonium. Bromide + 2.5% Glycerol | 625 | 19 |
| 0.1% Na₂ EDTA + 0.9% NaCl | 531 | 15 |
| 0.1% Na₂ EDTA + 2.5% Glycerol | 616 | 17 |
| 0.025% Polysorbate 80 + 0.9% NaCl | 440 | 25 |
| 0.025% Polysorbate 80 + 2.5% Glycerol | 600 | 18 |
| 2.5% Glycerol | 605 | 17 |
| 0.01% Benzalkonium Chloride + 4.5% Xylitol | 554 | 19 |
| 0.01% Benzalkonium Chloride + 5.4% Myoinositol | 584 | 19 |
| 0.01% Benzalkonium Chloride + 5.4% Mannitol | 570 | 21 | b. Prevention of Dry Skin (Irritation) Caused by 2% Sodium Lauryl Sulphate (Method: Modification of Sagiv et al. Skin Res. Technol. 6, 37, 2000)

Daily topical application of molar or isotonic polyols in deionized water, half an hour before application of 2% sodium lauryl sulphate in deionized water (SLS), on one of the two shaved flanks of guinea pigs, for three consecutive days, was examined in order to prevent SLS induced "Dry skin syndrome". Skin dryness and erythema were measured four days later in vivo:

| Name | Concentration | Corneometer | Mexameter |
|---|---|---|---|
| Glycerol | 1M | 5.5 ± 1.9 (E) | 4.1 ± 3.3 (E) |
| Glycerol | 0.3M | 25.9 ± 1.7 (NE) | 27.4 ± 2.2 (NE) |
| Xylitol | 0.3M | 2.8 ± 1.0 (E) | 0.2 ± 0.4 (E) |
| Myoinositol | 0.3M | 0.3 ± 1.1 (E) | 5.1 ± 0.9 (E?) |
| Mannitol | 0.3M | 2.2 ± 1.6 (E) | 1.7 ± 0.5 (E) |

Treatment of Dry Skin Induced by 2% Sodium Lauryl Sulphate (Sagiv et al, Skin Res. Technol. 6, 37, 2000)

| Name | Concentration | Corneometer | Mexameter |
|---|---|---|---|
| Glycerol | 1M | 3.2 ± 1.7 (E) | 1.5 ± 3.0 (E) |
| Glycerol | 0.3M | 3.3 ± 2.3 (E) | 21.2 ± 0.9 (NE) |
| Xylitol | 0.3M | 1.3 ± 1.1 (E) | 1.2 ± 0.9 (E) |
| Myoinositol | 0.3M | 0.7 ± 1.8 (E) | 1.0 ± 0.9 (E) |
| Mannitol | 0.3M | 1.4 ± 0.6 (E) | −0.1 ± 0.3 (E) |

E = Effective = No significant difference or little difference between the treated and untreated side.
NE = Not effective = Very much and significant difference between the treated and untreated side.

It was claimed that to be sure in efficacy both the "Corneometer" and "Mexameter" measurements have to be "Effective" (Sagiv et al. Skin Res. Technol. 6, 37, 2000).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

The invention claimed is:

1. A method for preventing or treating damage to skin cells caused by preservatives, detergents, drugs used in topical pharmaceutical compositions, drugs used in topical cosmetic compositions, or drugs used in topical veterinary compositions, said method consisting of:
   providing a composition that consists of an aqueous solution consisting of:
   5-18% (w/v) xylitol;
   5-10% (w/v) glycerol;
   at least one component selected from the group consisting of pharmaceutically acceptable excipients, preservatives, pH adjusting substances, and viscosity enhancing agents; and,
   the balance water;
   in the absence of any oil-in-water or wax-in-water emulsion;
   and,
   administering topically said composition to a patient in need thereof.

2. The method according to claim 1, wherein said composition is characterized by a pH of between 4.0 and 6.0.

3. The method according to claim 1, wherein said composition consists of an aqueous solution consisting of:
   5-18% (w/v) xylitol;
   5-10% (w/v) glycerol;
   a pH adjusting agent;
   a viscosity enhancing agent;
   at least one preservative; and,
   the balance water;

in the absence of any oil-in-water or wax-in-water emulsion.

4. The method according to claim 3, wherein said composition is characterized by a pH of between 4.0 and 6.0.

5. The method according to claim 1, wherein said viscosity enhancing agent is selected from the group consisting of polyacrylate 980 and polyacrylate 974.

6. The method according to claim 3, wherein said composition consists of an aqueous solution consisting of 5% (w/v) xylitol, 5% (w/v) glycerol, a pH adjusting agent, a viscosity enhancing agent, and at least one preservative.

7. The method according to claim 6, wherein said composition is characterized by a pH of between 4.0 and 6.0.

8. The method according to claim 1, wherein said composition consists of an aqueous solution consisting of 5-18% (w/v) xylitol, 5-10% (w/v) glycerol, a pH adjusting agent, and a viscosity enhancing agent.

9. The method according to claim 1, wherein said composition consists of an aqueous solution consisting of 5-18% (w/v) xylitol, 5-10% (w/v) glycerol, and a viscosity enhancing agent.

10. A method for prevention or treatment of irritation to skin cells, said method consisting of:
    providing a composition that consists of an aqueous solution consisting of:
    5-18% (w/v) xylitol;
    5-10% (w/v) glycerol;
    at least one component selected from the group consisting of pharmaceutically acceptable excipients, preservatives, pH adjusting substances, and viscosity enhancing agents; and,
    the balance water;
    in the absence of any oil-in-water or wax-in-water emulsion;
    and,
    administering topically said composition to a patient in need thereof.

11. The method according to claim 10, wherein said composition is characterized by a pH of between 4.0 and 6.0.

12. The method according to claim 10, wherein said composition consists of an aqueous solution consisting of:
    5-18% (w/v) xylitol;
    5-10% (w/v) glycerol;
    a pH adjusting agent;
    a viscosity enhancing agent;
    at least one preservative; and,
    the balance water;
    in the absence of any oil-in-water or wax-in-water emulsion.

13. The method according to claim 12, wherein said composition is characterized by a pH of between 4.0 and 6.0.

14. The method according to claim 10, wherein said viscosity enhancing agent is selected from the group consisting of polyacrylate 980 and polyacrylate 974.

15. The method according to claim 12, wherein said composition consists of an aqueous solution consisting of 5% (w/v) xylitol, 5% (w/v) glycerol, a pH adjusting agent, a viscosity enhancing agent, and at least one preservative.

16. The method according to claim 15, wherein said composition is characterized by a pH of between 4.0 and 6.0.

17. The method according to claim 10, wherein said composition consists of an aqueous solution consisting of 5-18% (w/v) xylitol, 5-10% (w/v) glycerol, a pH adjusting agent, and a viscosity enhancing agent.

18. The method according to claim 17, wherein said composition is characterized by a pH of between 4.0 and 6.0.

19. The method according to claim 10, wherein said composition consists of an aqueous solution consisting of 5-18% (w/v) xylitol, 5-10% (w/v) glycerol, and a viscosity enhancing agent.

* * * * *